United States Patent
Kosterev et al.

(10) Patent No.: US 7,248,611 B2
(45) Date of Patent: Jul. 24, 2007

(54) FREQUENCY SCANNING PULSED LASER HAVING SYNCHRONOUSLY SET SUBTHRESHOLD CURRENT

(75) Inventors: Anatoliy A. Kosterev, Houston, TX (US); Frank K. Tittel, Houston, TX (US)

(73) Assignee: William Marsh Rice University, Houston, TX (US)

( * ) Notice: Subject to any disclaimer, the term of this patent is extended or adjusted under 35 U.S.C. 154(b) by 835 days.

(21) Appl. No.: 10/284,781

(22) Filed: Oct. 31, 2002

(65) Prior Publication Data

US 2003/0127596 A1    Jul. 10, 2003

Related U.S. Application Data

(60) Provisional application No. 60/335,220, filed on Oct. 31, 2001.

(51) Int. Cl.
*H01S 3/00* (2006.01)
*H01S 3/13* (2006.01)

(52) U.S. Cl. .............................. 372/38.07; 372/29.015; 372/38.02

(58) Field of Classification Search ........... 372/29.015, 372/38.02, 38.07

See application file for complete search history.

(56) References Cited

U.S. PATENT DOCUMENTS

| 4,166,985 | A | * | 9/1979 | White et al. .................. 372/30 |
| 5,019,769 | A | * | 5/1991 | Levinson ..................... 372/31 |
| 5,936,987 | A | * | 8/1999 | Ohishi et al. .......... 372/29.014 |
| 6,037,832 | A | * | 3/2000 | Kaminishi .................. 327/538 |
| 6,400,744 | B1 | * | 6/2002 | Capasso et al. ............... 372/96 |

OTHER PUBLICATIONS

K. Namjou et al.; *Sensitive absorption spectroscopy with a room-temperature distributed-feedback quantum-cascade laser*; Optic Letters, vol. 23, No. 3, Feb. 1, 1998; (3 p.).

D. D. Nelson et al.; *Sub-part-per-billion detection of nitric oxide in air using a thermoelectrically cooled mid-infrared quantum cascade laser spectrometer*; Appl. Phys. B 75, 2002; (pp. 343-350).

* cited by examiner

*Primary Examiner*—Armando Rodriguez
(74) *Attorney, Agent, or Firm*—Conley Rose, P.C.

(57) ABSTRACT

The present invention provides methods and apparatus for flexible and reproducible control of quantum cascade laser frequency scans having short (nanosecond) pulse excitations. In accordance with a preferred embodiment of the invention, a method of digital frequency control for pulsed quantum cascade lasers includes digitally synthesizing a sub-threshold current, converting the sub-threshold current to analog form, and generating laser pulses. Preferably, the sub-threshold current is synchronized to the laser pulses.

17 Claims, 4 Drawing Sheets

FREQUENCY SCANNING PULSED LASER HAVING SYNCHRONOUSLY SET SUBTHRESHOLD CURRENT

This application claims priority to U.S. Provisional Application Ser. No. 60/335,220, entitled "Synchronized Computer Control for Pulsed Quantum Cascade Laser Frequency Scanning," filed on Oct. 31, 2001 and incorporated herein by reference.

BACKGROUND

Infrared laser absorption spectroscopy is an extremely effective tool for detecting trace gases. The demonstrated sensitivity of this technique is at the parts per billion (ppb) level. Presently, the usefulness of the laser spectroscopy approach is limited by the availability of convenient tunable sources in the spectroscopically important "fingerprint" region from 3 to 20 μm. The available options include cryogenically cooled lead salt diode lasers and coherent sources based on difference frequency generation (DFG). Sensors based upon lead salt diode lasers are typically large in size and require consumables because the diodes operate at temperatures below 90 K. DFG based sources (especially PPLN based) are shown to be very robust, but they generate inherently low IR power. DFG based sensors are suitable for many atmospheric monitoring applications. However, their spectral coverage is currently limited to wavelengths shorter than 5 μm by the optical transparency of suitable nonlinear optical crystals such as periodically poled $LiNbO_3$.

The recent development of quantum cascade lasers with distributed feedback (QC-DFB) fabricated by band structure engineering offer an attractive option for IR absorption spectroscopy. Compared to Pb-salt diode lasers, QC-DFB lasers allow the realization of very compact narrow-linewidth mid-IR sources combining single-frequency operation and substantially higher powers (tens of mW) at mid-IR wavelengths (3.5 to 24 μm). Pulsed DFB QC lasers are semiconductor lasers able to emit mid-IR radiation at room temperature (continuous wave, or "cw", operation requires temperatures below 150K at this time). The higher power of QC lasers permits the use of advanced detection techniques that improve S/N ratio of trace gas spectra and decrease the apparatus size. For example in Cavity Enhanced Spectroscopy (CES) and Cavity Ringdown Spectroscopy (CRDS) an effective absorption pathlength of hundreds of meters can be obtained in a laptop-size device. The large wavelength coverage available with QC lasers allows numerous molecular trace gas species to be monitored. Recent measurements with QC-DFB lasers have demonstrated the usefulness of these devices for sensitive, highly selective real time trace gas concentration measurements based on absorption spectroscopy with sensitivities of several parts per billion (See K. Namjou et al, "Sensitive absorption spectroscopy with a room-temperature distributed-feedback quantum-cascade laser", Optics Letters, V. 23, n. 3, Feb. 1, 1998, which is hereby incorporated by reference).

Pulsed operation of QC-DFB lasers gives a unique opportunity to design a liquid nitrogen-free mid-IR spectroscopic sensor. However, specific problems are associated with this mode of operation. The peak power in pulsed mode is essentially the same as for cw operation, but the duty cycle has to be less then 1 percent to avoid an overheating of the device. Therefore, the average power is less than the power generated by the cw operation. This difference requires either more sensitive detection of average power or gated detection of peak power. Another problem is laser frequency chirping during the current pulse. This effect causes broadening of laser linewidth, limiting the spectral resolution and complicating data processing. These features associated with pulsed operation should be considered in the design of a trace gas sensor.

SUMMARY

There is disclosed herein a system and method for performing a spectroscopic analysis. In one embodiment, the system comprises a laser and a digital controller. The laser receives an excitation signal having a subthreshold component and a pulsed component. The digital controller may provide the subthreshold component and preferably assures that the subthreshold component changes synchronously with pulses in the pulsed component. The subthreshold current is preferably held constant for a predetermined delay before the pulse occurs. The subthreshold current may be incremented in a fashion that provides a linear frequency sweep, thereby simplifying the ultimate spectroscopic analysis. Potential benefits of the disclosed system may include improved spectroscopic data acquisition such as linearization of frequency scans performed with quantum cascade lasers, derivative spectroscopy to exclude low-frequency noise, and active frequency stabilization using a digital feedback loop.

BRIEF DESCRIPTION OF THE DRAWINGS

For a more detailed description of the preferred embodiment of the present invention, reference will now be made to the accompanying drawings, wherein.

DETAILED DESCRIPTION OF PREFERRED EMBODIMENTS

Pulsed QC-DFB Laser Prototype

Figure 1:
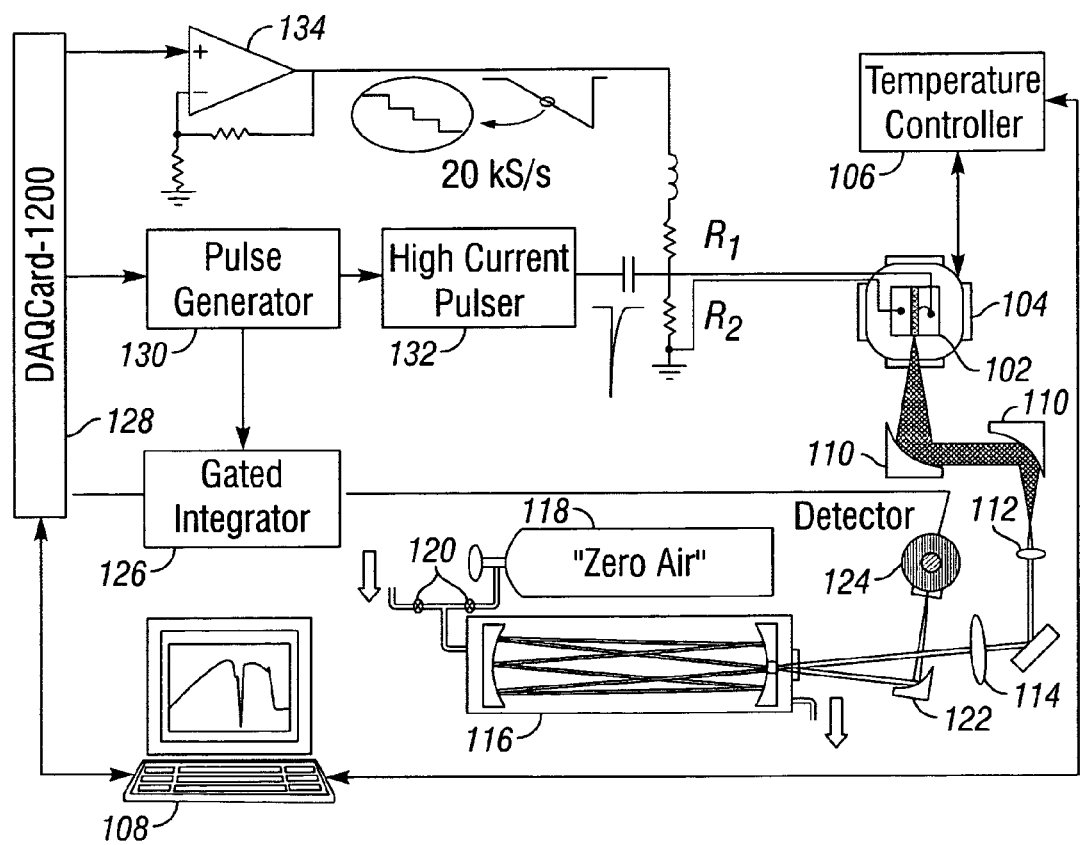
FIG. 1 is a schematic of a prototype pulsed QC-DFB laser based gas sensor configuration.

A schematic of the prototype pulsed QC-DFB laser-based gas sensor configuration is shown in FIG. 1. A QC-DFB laser 102 designed for pulsed near-room temperature operation at ~8 μm was mounted on a three-stage thermoelectric cooling module inside a compact (about 75×75×75 mm$^3$), evacuated housing 104. The thermoelectric cooling module was driven by a temperature controller 106 (which may be a Wavelength Electronics LFI-3751) communicating with a laptop computer 108 through a RS232 serial communication port. The temperature of the QC-DFB laser 102 could be varied from −40° C. to above room temperature. In practice, the laser temperature was usually kept below +6° C. because of a rapid decrease in laser power, an increase of threshold current and the appearance of mode instabilities at higher temperatures.

The laser light was collected and shaped into a narrow parallel beam by two off-axis parabolic mirrors 110 and an uncoated $BaF_2$ lens 112. An additional lens 114 with f=500 mm was used to focus the beam on the entrance aperture of a 100-m path-length multi-pass cell 116 (New Focus Model 5612). To obtain absorption spectra, a "zero-air" rapid background subtraction technique was employed: the spectrum of nonabsorbing ultrapure nitrogen from cylinder 118 was subtracted from the spectrum of the gas sample being studied. The gas exchange was obtained by use of a pressure controller in combination with an electromagnetically actuated three-way valve 120. After exiting the multipass cell 116, the IR radiation was collected with a small off-axis parabolic mirror 122 and detected with a liquid nitrogen cooled photovoltaic HgCdTe detector 124 with a built in preamplifier (20-MHz bandwidth). Other detectors may alternatively be employed, including a Peltier-cooled detector. The detector signal was measured with a gated integrator 126 (Stanford Research Systems SR-250) and a 12-bit data acquisition card 128 (National Instruments DAQCard-1200) coupled to laptop computer 108. An integration window of 15 ns was set to integrate the signal at the peak of ~35 ns full-width at half-maximum detector response. The useful signal was separated in time from any interfering scattered light due to a 330 ns delay of the laser pulse in the multipass cell.

Figure 2A:
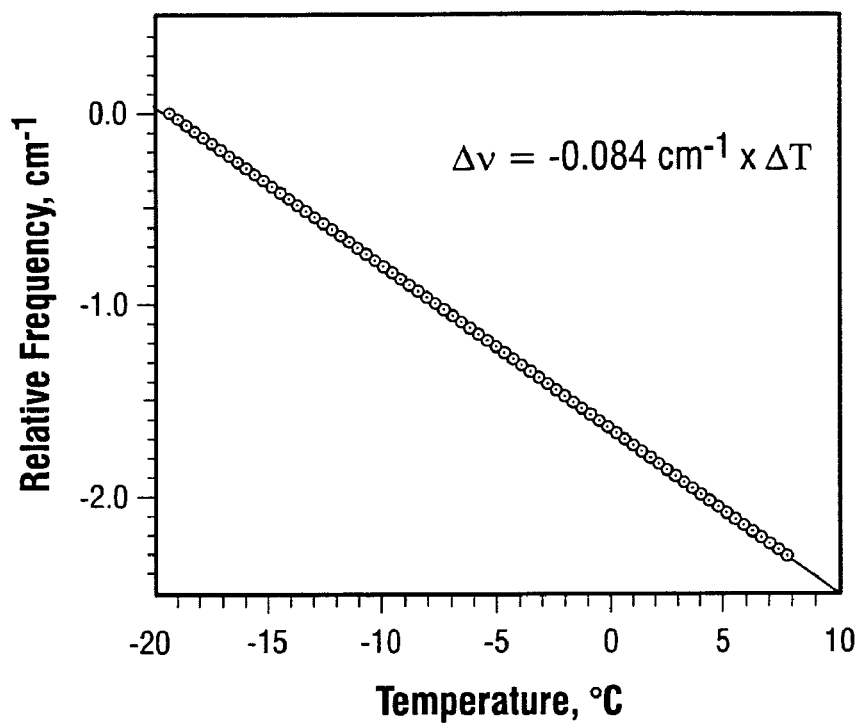
FIGS. 2A and 2B are graphs showing the frequency calibration curves for slow and fast laser scans, respectively.
Figure 2B:
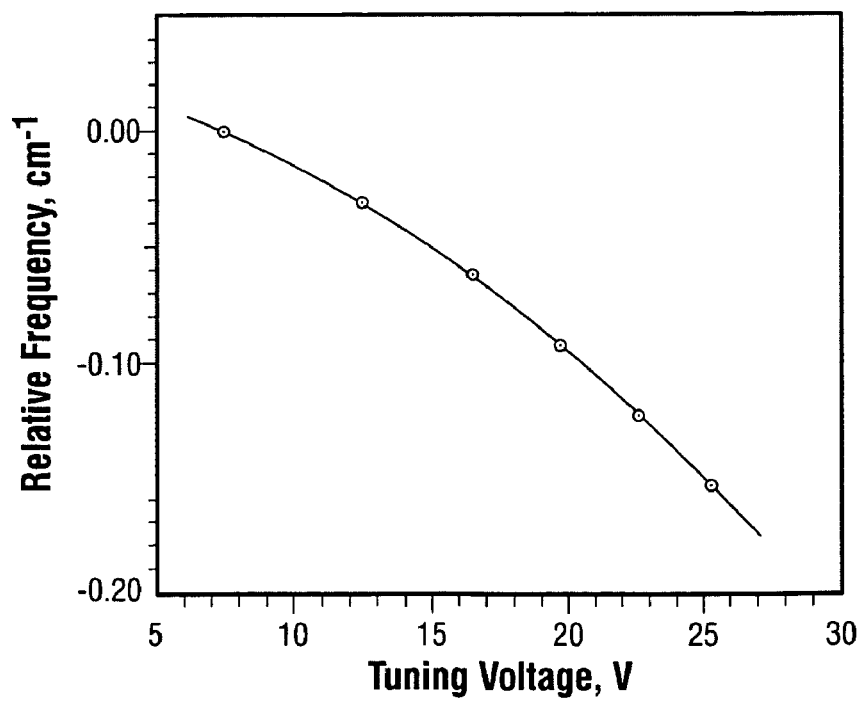

Short current pulses (~5 ns full-width at half-maximum) were generated by pulse generator 130, amplified to high current by pulser 132, and supplied to the laser through a low-impedance stripline. The pulse repetition rate was limited to 20 kHz by the minimum acquisition time of the gated integrator. A variable offset of computer-controlled sub-threshold current was added to each pulse, enabling "fast" wavelength tuning. The current offset was created by amplifier 134, which amplifies a computer-synthesized voltage from the D/A converter of the data acquisition card (DAQC) 128. The current offset was applied to the laser through a decoupling resistor $R_1=50\Omega$. Computer control adds flexibility to the device architecture, enabling arbitrary waveforms to be applied. It was discovered that when the sub-threshold current exceeded 230 mA, the laser operation became unstable. This effect limited fast laser tunability to ~0.23 cm$^{-1}$. Slow laser frequency tuning was performed by changing the laser temperature. Variation of the laser temperature from −25° C. to +5° C. allowed tuning in a spectral range from ~1255.5 to 1258.0 cm$^{-1}$. Frequency calibration curves for slow and fast laser scans are shown in FIGS. 2A and 2B, respectively. These data are obtained using the interference fringes produced by two air-separated uncoated ZnSe surfaces. The slow scan is linear with a coefficient of −0.084 cm$^{-1}$/° C. The solid line in FIG. 2B shows a third order polynomial fit.

A compact pulser module 130 with a fixed pulse duration of ~5 ns was used in the present laser spectrometer design to minimize the heating-related laser frequency chirp. It was connected to the laser with a high-frequency low-impedance stripline. A coupling resistor $R_2=7.9\ \Omega$ was connected to the stripline in order to suppress electrical oscillations in the circuit. The correct choice of $R_2$ is of some importance in determining the spectral properties of the laser radiation. The use of this resistance was found to ensure a significantly smaller laser linewidth (2×) at the same or even higher laser power levels.

Figure 3:
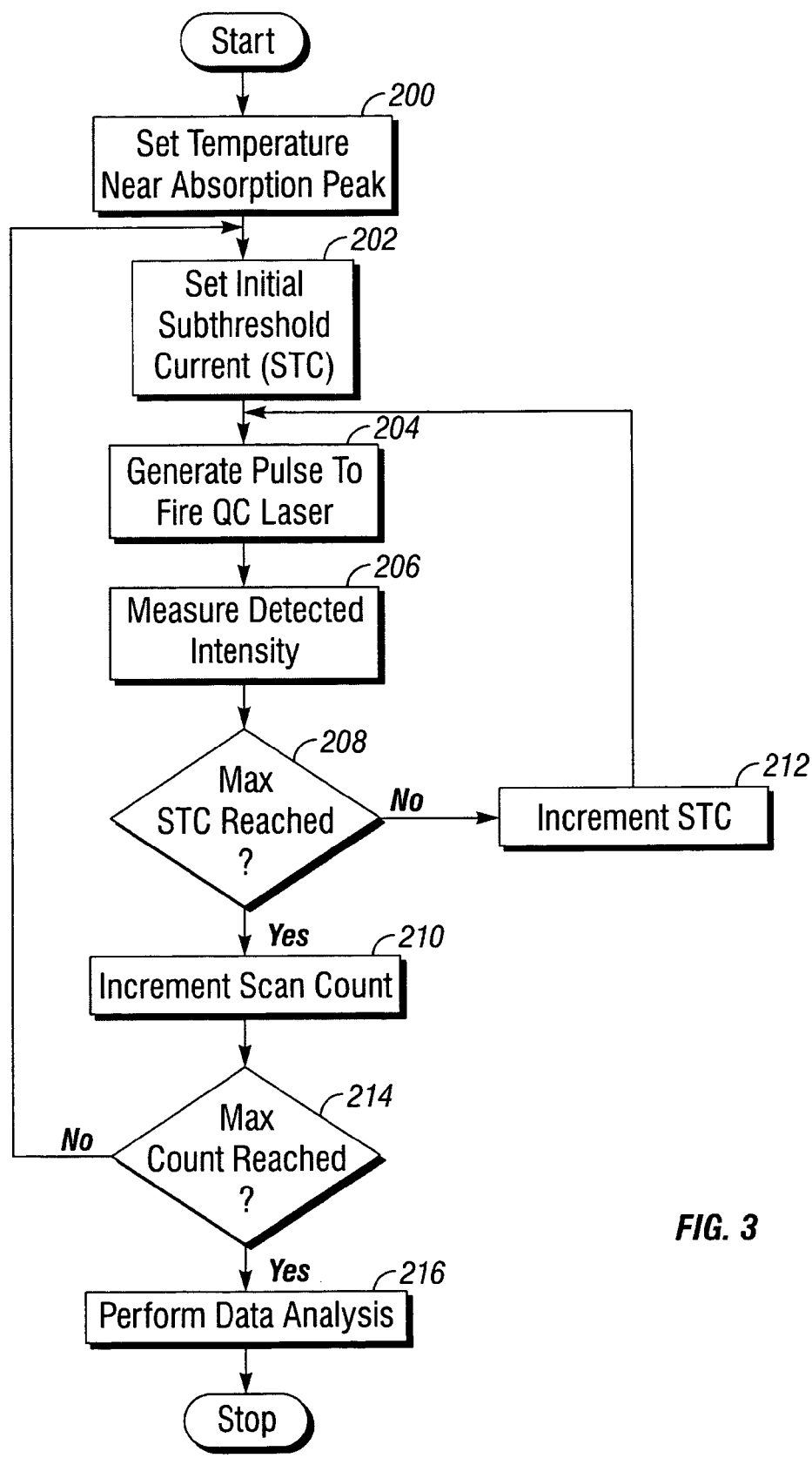
FIG. 3 is a block diagram of an algorithm in accordance with one embodiment of the present invention.

Referring now to FIG. 3, a block diagram of a fast-scan data acquisition algorithm in accordance with the present invention is shown. Initially, the user sets the laser temperature so the laser operates near an absorption line of interest (block 200). The user then sets the initial sub-threshold current (STC) (block 202). While the initial sub-threshold current may be entered manually, it is preferably computer synthesized or computer generated. Also, the subthreshold current preferably mimics a non-return-to-zero (NRZ) pattern, where the current incrementally increases at a predetermined rate until a predetermined maximum is reached.

Next, the pulse generator is triggered by the DAQC to fire the laser (block 204). A predetermined instrument (e.g. a computer) detects the intensity of each laser pulse individually (block 206). In some embodiments, the intensity of each laser pulse is measured, digitized, and stored in computer memory for later analysis.

If the maximum sub-threshold current has not been reached (block 208), the subthreshold current is incremented in block 212 and control returns to block 204. Blocks 204, 206, 208, and 212 are repeated until the maximum sub-threshold current is reached. Once the maximum is reached, a scan count is incremented (block 210) and a test is performed in block 214 to determine whether a predetermined number of scans have been performed. If not, control returns to block 202 where the subthreshold current is reset and another scan is initiated. Once the desired number of scans have been performed, then a data analysis of the collected data is performed in block 216.

In a preferred embodiment, the initial subthreshold current and maximum subthreshold current are chosen to provide a desired frequency range, and the subthreshold increment is chosen to provide a desired resolution with the frequency range. For example, each scan may cover 512 subthreshold current values, which may be chosen so as to provide 512 equally-spaced frequencies. In some embodiments, it may be desirable to repeat the scans continuously and average the data until the predetermined maximum number of scans is reached. Also, in a preferred embodiment, the laser pulses are generated at a predetermined time following the subthreshold current's incremental increases, thus allowing the subthreshold current to "settle" before initiating a laser pulse.

Figure 4:
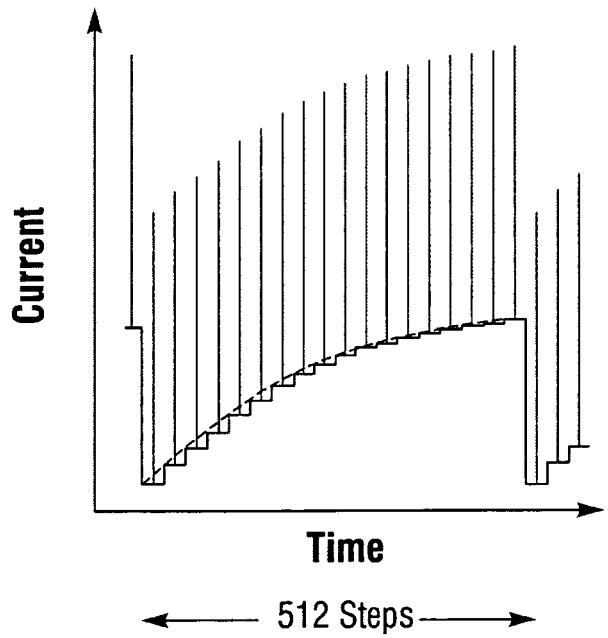
FIG. 4 is a schematic of an excitation current which may be provided by the algorithm of FIG. 3.

Referring now to FIG. 4, an example of the excitation current provided to the laser in accordance with the algorithm of FIG. 3 is shown. The excitation current comprises a subthreshold current component, which is seen as "steps" in the excitation current, and a pulsed current component, which is seen as "spikes" or "peaks" on each of the steps. While each of the spikes is shown in the center of each step, the spikes may be located on any part of the steps. Also, while each spike has a corresponding step, any predetermined number of spikes may be associated with each step. In an alternative embodiment, the subthreshold current "steps down" as a function of time rather than increasing. In yet another embodiment, the subthreshold current alternately increments and decrements with each scan cycle to avoid sudden, large changes in the subthreshold current.

Referring back to FIG. 2B, the laser frequency exhibits an essentially nonlinear dependence on the offset voltage applied to the stripline. This nonlinearity is preferably taken into account when generating the subthreshold current component so as to make the laser frequency vary linearly from pulse to pulse, i.e. linearly with respect to data point number during each scan.

To characterize the spectral properties of the laser pulses, the laser temperature was set to −8.5° C. to enable a fast-scan across the $CH_4$ absorption line at 1256.601 cm$^{-1}$. The laser pulses were detected after passing through a 3 cm long cell that was alternatively filled with 1.25 Torr of $CH_4$ or evacuated. From this spectrum it was concluded that the laser lineshape is close to the Fourier-transform of a 3.1 ns long rectangular pulse on a broad pedestal that is due to the frequency chirping. The FWHM of the narrow spectral peak is $9.5\times10^{-3}$ cm$^{-1}$, or 290 MHz. The laser lineshape thus acquired describes the instrument function of the laser spectrometer and was used in processing the absorption spectra described below.

This data acquisition technique was applied to detect $CH_4$ and $N_2O$ in ambient air using a 100 m pathlength optical multipass cell. To enhance the accuracy of measurements, a "zero-air" subtraction technique was employed. The laser temperature was set to −8.5° C. to detect a $CH_4$ absorption line at 1256.601 $cm^{-1}$, and to −6.2° C. to detect an $N_2O$ absorption line at 1256.371 $cm^{-1}$. Both spectra were acquired at 85 Torr air pressure in the multipass cell. The baseline, or "no absorption" line, of the acquired data exhibit some slow variations, despite the use of the zero-air technique. It is believed that this is due to acoustic vibrations of the optical table that lead to small displacements of the laser beam. This was confirmed by a spectral analysis of the noise, which indicated a strong 90 Hz component correlating with optical table vibrations.

Gas Detection and Interpretation

In order to determine the concentrations of absorbing species, the following procedure was applied:
(1) The acquired spectra were numerically differentiated by subtracting a shifted array of the same data. This resulted in suppressing the baseline offset and slow baseline variations and gave a Dataset 1;
(2) The absorption of air in the cell at 85 Torr was simulated using the HITRAN database, and this spectrum was convolved with the laser spectrometer instrument function;
(3) The resulting simulated absorption spectrum was numerically differentiated as in step (1) giving a Dataset 2; and
(4) Each number of the Dataset 1 was plotted as a function of the corresponding number of the Dataset 2, and a linear regression analysis was applied to define the ratio of two absorption lines. This ratio was obtained as a slope of the linear fit.

This algorithm was applied to determine the concentrations of $CH_4$, HDO and $N_2O$ in air. The methane concentration is in a good agreement with previous measurements in the Houston area. Absorption of HDO, when compared to the HITRAN data, gives a relative humidity of 49%, which is lower than the hygrometer readings of 60%. However, the isotopic abundance of deuterium assumed in this database is 10% to 30% higher than in natural atmospheric water vapor, and this explains the deviation of the humidity calculated from the HDO absorption and the hygrometer readings. The concentration of $N_2O$ was found to match the standard air value. The calculated standard deviation of the fitting line slope for all three absorption lines corresponds to a minimum detectable absorption of $3 \times 10^{-4}$ when averaging over 200 scans (15 sec) and $1.7 \times 10^{-4}$ for 1000 scans.

In order to cover a larger frequency range in a single laser scan, slow temperature scanning is required. The simplest technique of acquiring such spectra consists of a slow continuous change of the laser temperature while periodically measuring the absorption of the laser pulses in the gas sample. When such measurements were carried out it was found that low-frequency noise is present in the acquired spectra with a peak-to-peak magnitude corresponding to ~1% absorption. This noise was mainly due to acoustic vibrations of the laboratory table. To eliminate the low-frequency noise, the algorithm of FIG. 3 was applied to acquire the digital second derivative by means of fast laser frequency cycling. It was determined that the noise of the second derivative signal did not depend noticeably on the temperature (and laser intensity) and also did not change when the laser beam was blocked. This confirms that the low-frequency noise was efficiently suppressed by applying the proper subthreshold waveform and data processing.

An estimate of the number of laser pulses N involved in the measurements of a single absorption line was made. An addition of uncorrelated fluctuations in quadrature when the derivative is calculated was also taken into account. This evaluation gave a four times lower N value for a slow scan than for a 200 times averaged fast scan. Hence, the detection limit normalized to $\sqrt{N}$ is the same for fast and slow scans. The sensitivity for both modes of spectral measurements is limited by random errors of the measuring electronics.

Figure 5:
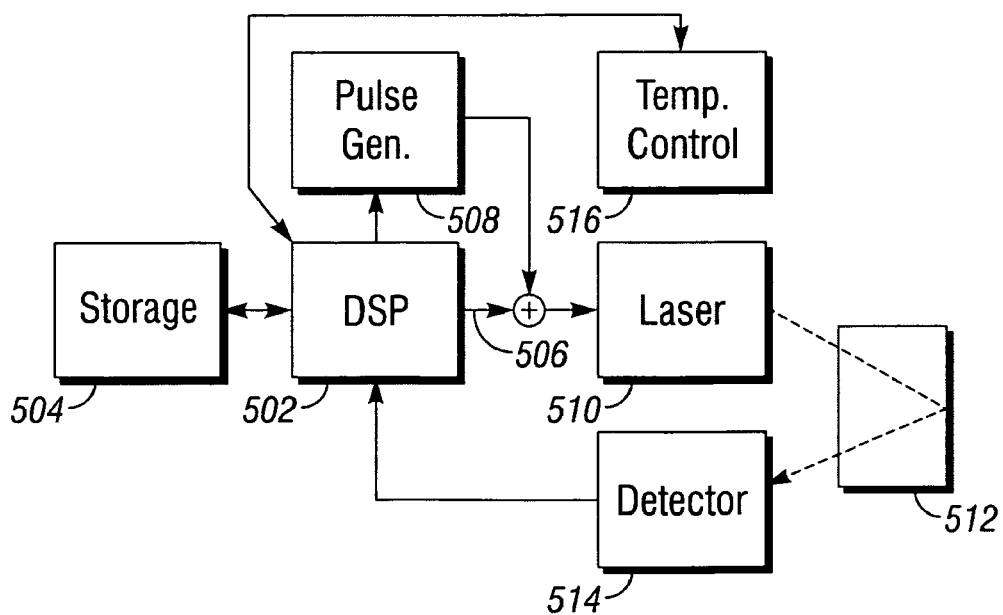
FIG. 5 is a schematic a preferred embodiment.

Referring now to FIG. 5, a preferred spectroscopic sensor embodiment is shown. A digital signal processor (DSP) 502 is coupled to a storage module 504 to retrieve and execute pre-programmed instructions. The storage module may take the form of integrated-circuit memory, magnetic storage media, optical storage media, some other method of information storage, or any combination thereof. The storage module 504 is preferably also configured to store data from intermediate calculations by the DSP and data for final results to be delivered to a user or external computer system. The storage module 504 may additionally store adjustable parameters for tailoring the operation of the sensor embodiment.

In accordance with the pre-programmed instructions, the DSP 502 preferably provides a stepped subthreshold current component signal 506. The DSP preferably also configures a pulse generator to generate a pulsed current component signal that is added to the subthreshold current component signal to form an excitation signal for laser 510. The DSP is preferably also configured to monitor and adjust the operating temperature of laser 510 via temperature controller 516.

In response to the excitation current, the laser 510 preferably generates a sequence of laser pulses that vary linearly in frequency (and hence, wavelength). The laser pulses pass through a sample space 512 which includes a sample to be spectroscopically analyzed, and reaches an intensity detector 514. The DSP 502 preferably determines the received intensity of each laser pulse and preferably associates a frequency with the pulse as determined by the digitally-controlled subthreshold current. The DSP 502 preferably processes the frequency and intensity information with information from previous and/or subsequent measurements to determine a frequency spectrum associated with the sample. The DSP 502 may store this frequency spectrum information. Alternatively, the DSP 502 may proceed with a programmed spectrum analysis technique to derive information of interest regarding the sample.

While the preferred embodiments of the invention have been shown and described, modifications thereof can be made by one skilled in the art without departing from the spirit and teachings of the invention. The embodiments described herein are exemplary only, and are not intended to be limiting. Many other variations and modifications of the invention disclosed herein are possible and are within the scope of the invention. The disclosures of all publications, patents and patent applications cited above are hereby incorporated herein by reference.

What is claimed is:

1. A system for spectroscopic analysis that comprises:
a laser configured to receive an excitation signal having a subthreshold current component and a pulsed current component, wherein the laser has a subthreshold current frequency dependence;

a digital controller that provides the subthreshold current component, wherein the digital controller alters the subthreshold current component in synchronization with pulses in the pulsed current component.

2. The system of claim 1, further comprising:

a pulse generator that provides the pulsed current component to the laser.

3. The system of claim 2, wherein the digital controller triggers the pulse generator a predetermined time after changing the subthreshold current.

4. The system of claim 1, further comprising:

a detector configured to measure a received intensity of a light pulse from the laser, wherein the digital controller is coupled to the detector to receive the received intensity measurements.

5. The system of claim 4, wherein the digital controller associates a respective frequency with each received intensity measurement, the respective frequency determined by the associated subthreshold current value.

6. The system of claim 5, wherein the digital controller iteratively increments the subthreshold current so as to obtain a received intensity measurement at each of a set of linearly spaced frequencies.

7. The system of claim 6, wherein the digital controller repeats intensity measurements at each frequency in the set of linearly spaced frequencies and combines measurements at each frequency.

8. The system of claim 1, further comprising:

a temperature controller coupled to the laser, and configured to maintain the laser at an operating temperature specified by the digital controller; and a storage module coupled to the digital controller and configured to store program instructions to be executed by the digital controller.

9. A method that comprises:

generating a pulsed current signal having a series of current pulses;

generating a digitally-controlled subthreshold current signal having a series of discrete current values that change synchronously with the series of pulses;

combining the pulsed current signal with the digitally controlled signal to produce an excitation signal; and providing the excitation signal to a laser.

10. The method of claim 9, further comprising:

detecting a received intensity of each pulse from the laser; and associating a subthreshold-current-determined frequency with each pulse.

11. The method of claim 10, wherein each pulse in a scan period is associated with a unique discrete current value, and each discrete current value is associated with only one pulse.

12. The method of claim 10, wherein the frequency changes linearly with each pulse.

13. A method of detecting trace components of a gas, the method comprising:

generating a digitally-controlled sequence of subthreshold current values in a subthreshold component signal;

generating a pulse component signal having a sequence of pulses, wherein each pulse is generated a predetermined time after a change to the subthreshold component signal;

combining the pulse component signal with the subthreshold component signal to form an excitation signal; and applying the excitation signal to a laser.

14. The method of claim 13, further comprising:

detecting a received intensity of each pulse from the laser after the pulse has interacted with the gas, wherein the received intensities are associated with discrete frequencies so as to form a characteristic spectrum of the gas.

15. The method of claim 14, further comprising:

differencing the characteristic spectrum of the gas with a baseline spectrum; and determining amplitudes associated with characteristic frequencies of selected trace elements.

16. The method of claim 13, wherein the laser is a quantum cascade laser with distributed feedback.

17. The method of claim 13, further comprising:

setting an operating temperature of the laser; and performing a calibration analysis to determine a baseline spectrum.

* * * * *